(12) United States Patent
Hammond

(10) Patent No.: US 8,926,791 B2
(45) Date of Patent: Jan. 6, 2015

(54) WASTEWATER SLUDGE TREATMENT DEVICE

(71) Applicant: Gary Hammond, Leesburg, FL (US)

(72) Inventor: Gary Hammond, Leesburg, FL (US)

(*) Notice: Subject to any disclaimer, the term of this patent is extended or adjusted under 35 U.S.C. 154(b) by 30 days.

(21) Appl. No.: 13/745,266

(22) Filed: Jan. 18, 2013

(65) Prior Publication Data

US 2014/0202222 A1    Jul. 24, 2014

(51) Int. Cl.
*B01D 1/00*  (2006.01)
*C05F 3/04*  (2006.01)
*A61L 2/04*  (2006.01)

(52) U.S. Cl.
CPC .... *C05F 3/04* (2013.01); *A61L 2/04* (2013.01)
USPC ............ 159/1.1; 202/234; 202/270; 210/153; 210/167.07; 210/175

(58) Field of Classification Search
USPC .................... 159/1.1; 202/270, 234; 210/153, 210/167.07, 175; 71/11, 12, 23
See application file for complete search history.

(56) References Cited

U.S. PATENT DOCUMENTS

| | | | | |
|---|---|---|---|---|
| 4,373,308 | A * | 2/1983 | Whittaker | 52/173.3 |
| 7,745,723 | B2 * | 6/2010 | Dyson et al. | 136/246 |
| 8,122,878 | B1 * | 2/2012 | Gross et al. | 126/600 |
| 8,256,382 | B2 * | 9/2012 | Ba-Abbad | 119/450 |
| 2011/0315542 | A1 * | 12/2011 | Ba-Abbad et al. | 204/157.6 |

* cited by examiner

*Primary Examiner* — Nina Bhat

(57) ABSTRACT

A tank or bed has a plurality of sidewalls that create a bed cavity and a Fresnel panel frame that includes at least one Fresnel panel. The Fresnel panel frame may be adjacent to the bed cavity and may cover at least a portion of the bed cavity. An amount of sludge may be contained within the bed cavity. When placed in sunlight, the heat enhanced by the Fresnel panels may heat the sludge sufficiently for the sludge to be used as fertilizer.

9 Claims, 4 Drawing Sheets

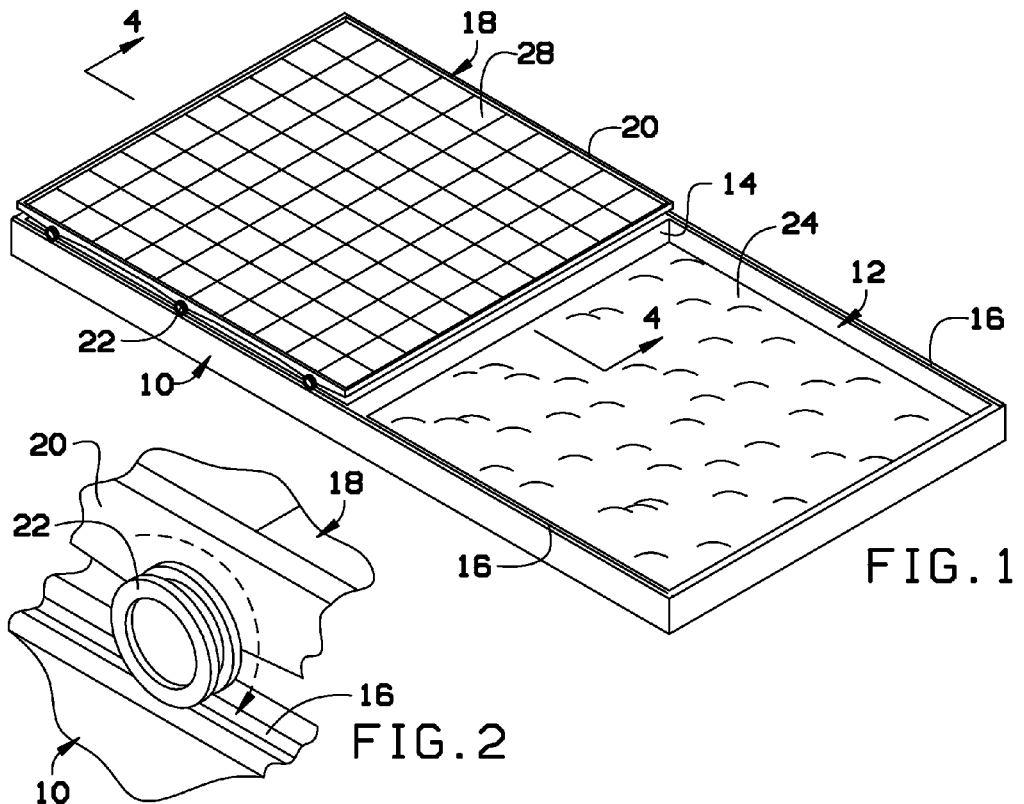
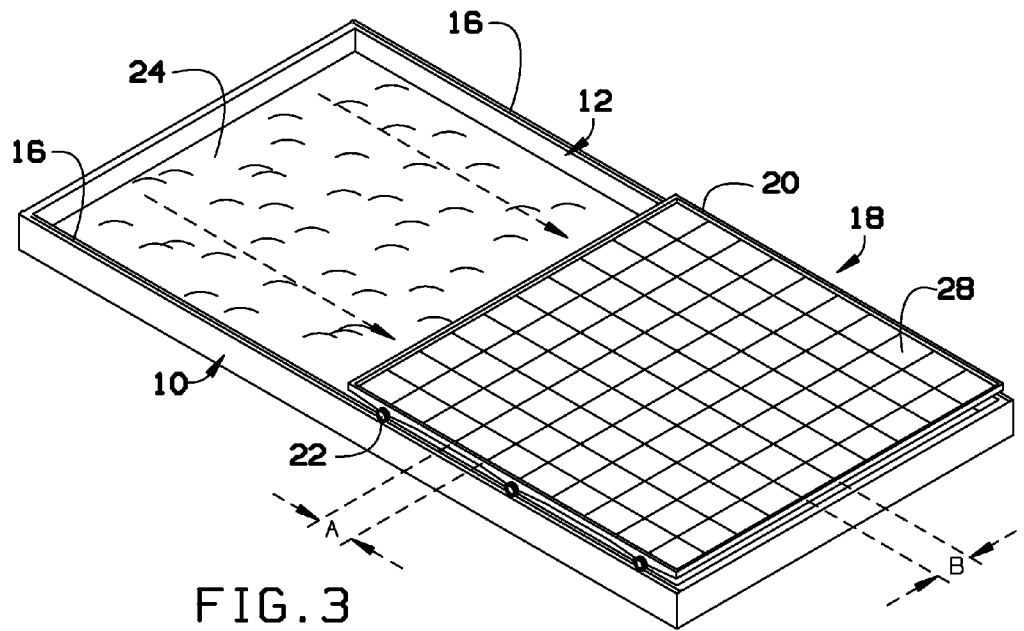

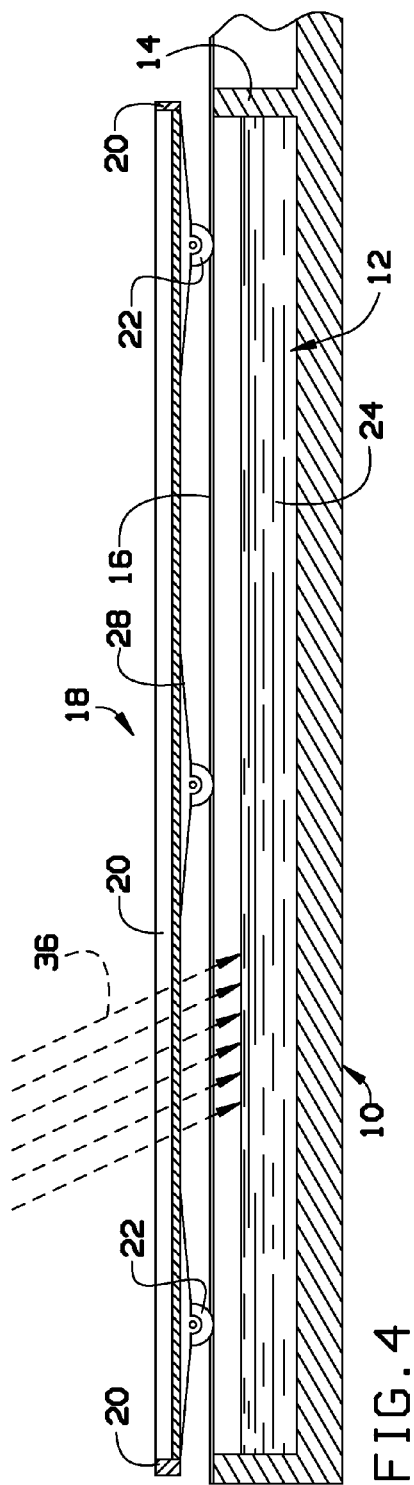
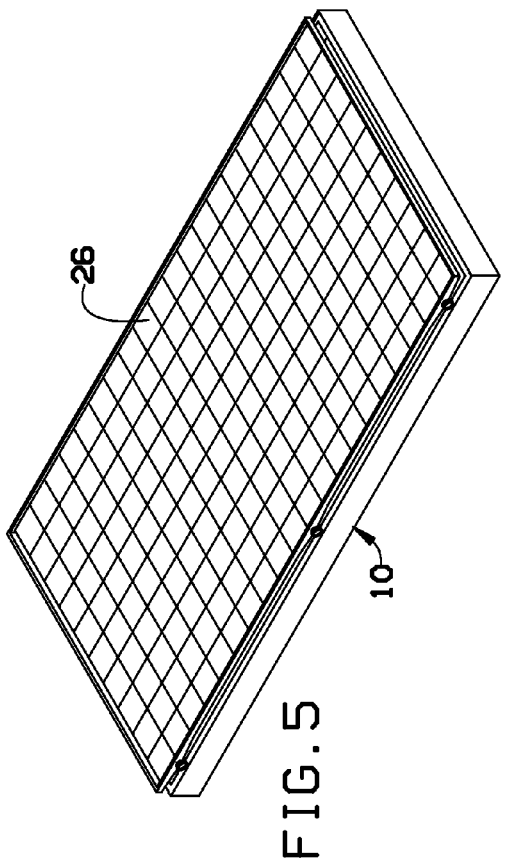

WASTEWATER SLUDGE TREATMENT DEVICE

BACKGROUND OF THE INVENTION

The present invention relates to sludge treatment device and, more particularly, to a sludge treatment device that turns sludge into safe to use fertilizer.

After the treatment of wastewater is performed, biosolids and the associated contaminants are removed. However, biosolids are typically high in organic content and contain moderate amounts of nutrients such as nitrogen and phosphorus. These properties make biosolids valuable as a fertilizer or soil amendment.

Biosolids are the solid, semisolid, or liquid residue generated during the biological wastewater treatment process. Biosolids that are used beneficially must be treated to reduce pathogens and vector attraction. Distribution and marketing of Class AA biosolids products is regulated by governments. Class AA biosolids are considered to be the highest quality of biosolids produced and may be utilized as fertilizer through commercial distribution and marketing.

To achieve a Class AA status, the biosolids must be treated to a level that essentially eliminates pathogens and meets strict parameter concentration limits for heavy metals. Class AA biosolids may be distributed in bulk or bagged for sale at retail garden centers. Class AA biosolids may be marketed in different physical forms, and, like traditional commercial fertilizer products, are not subject to site management restrictions if the product is registered as a fertilizer or distributed and marketed to a person or entity that will sell or give-away the biosolids or biosolids products as a fertilizer.

There are generally two classes of biosolids recognized in the United States Environmental Protection Agency's (EPA) regulations: Class B pathogen reduction standards, as set forth in 40 CFR 503, which require a fecal coliform level of less than two million most-probable-number (MPN) per gram of total solids, and Class A pathogen standards per 40 CFR 503. EPA's Class A pathogen standards requirements are met in biosolids when fecal coliform densities are less than 1,000 MPN per gram total solids; or when *Salmonella* densities are less than 3 MPN per four grams total solids. Additionally, enteric virus must be less than 1 plaque-forming unit per four grams of total solids, and helminth ova is less than one viable helminth ova per four grams of total solids.

Traditionally, biosolids (sludge) disposal involves trucking the sludge into rural areas and dumping the sludge onto fields. This may cause major health concerns. Other methods of disposal may include incineration, adding chemicals or dumping into landfills. However, concerns about contaminants, runoff, air pollution, tipping fees, and rising transportation costs have resulted in cities and municipalities seeking alternative and more efficient methods to handle the removal of wastewater biosolids.

SUMMARY OF THE INVENTION

Others have attempted various methods of biosolid pasteurization, but each method has shortcomings. For example, solar drying in greenhouses does not dry or heat sewage sludge and septic waste to a safe level. Gas drying or alkaline stabilization have high processing costs for energy, fuel and chemicals.

As can be seen, there is a need for processes and apparatus for treatment of biosolids. It is also desirable that the treatment can process liquid landfill leachate, by quickly evaporating the leachate which will eliminate transportation and disposal costs of the leachate to an industrial wastewater treatment facility. It is desirable that these processes remove or reduce pathogens in cake or liquid sludge through the use of Fresnel lens solar heat, time, and certain process conditions. It is desirable that these processes reduce most costs of disposal by reducing the expense of paying commercial disposal companies for disposal of the sludge. It is also desirable that the processes use sunlight to generate the heat for drying and pasteurization of the biosolids.

In one aspect of the present invention, an apparatus for changing sludge into fertilizer comprising: a bed having a plurality of walls comprising a first sidewall, a second sidewall, a first end wall and a second end wall, wherein the plurality of walls create a bed cavity and the bed cavity is configured to hold sludge; and a Fresnel panel frame comprising at least one Fresnel panel wherein the Fresnel panel frame is located adjacent to the plurality of walls and covers at least a portion of the bed cavity.

In another aspect of the present invention, the Fresnel panel frame comprises a plurality of panels.

In another aspect of the present invention, at least one bed cavity divider wall within the bed cavity creating at least two compartments within the bed cavity.

In another aspect of the present invention, a Fresnel sliding panel assembly is provided.

In another aspect of the present invention, the Fresnel sliding panel assembly comprises: a bed rail on the top edge of the first sidewall and the second sidewall; and a roller wheel attached to the Fresnel panel frame, wherein the roller wheel aligns with and rests within the bed rail.

In another aspect of the present invention, the at least one Fresnel panel is at least one spot Fresnel panel.

In another aspect of the present invention, the at least one Fresnel panel is at least one linear Fresnel panel.

In another aspect of the present invention, a trailer bed supporting the bed of the apparatus is provided.

In another aspect of the present invention, a method of treating sludge comprising: loading sludge into the bed cavity; covering the bed cavity and the sludge with the Fresnel panel frame; and allowing the sun to shine through the Fresnel panel frame and thereby heating the sludge.

These and other features, aspects and advantages of the present invention will become better understood with reference to the following drawings, description and claims.

BRIEF DESCRIPTION OF THE DRAWINGS

FIG. 1 is a perspective view of the invention shown in use;

FIG. 2 is a detail perspective view of the invention;

FIG. 3 is a perspective view of the invention illustrated with item 18 Fresnel sliding panel shown in translated configuration;

FIG. 4 is a section detail view of the invention along line 4-4 in FIG. 1;

FIG. 5 is a perspective view of an alternate embodiment of the invention;

DETAILED DESCRIPTION OF THE INVENTION

Figures 6, 7:
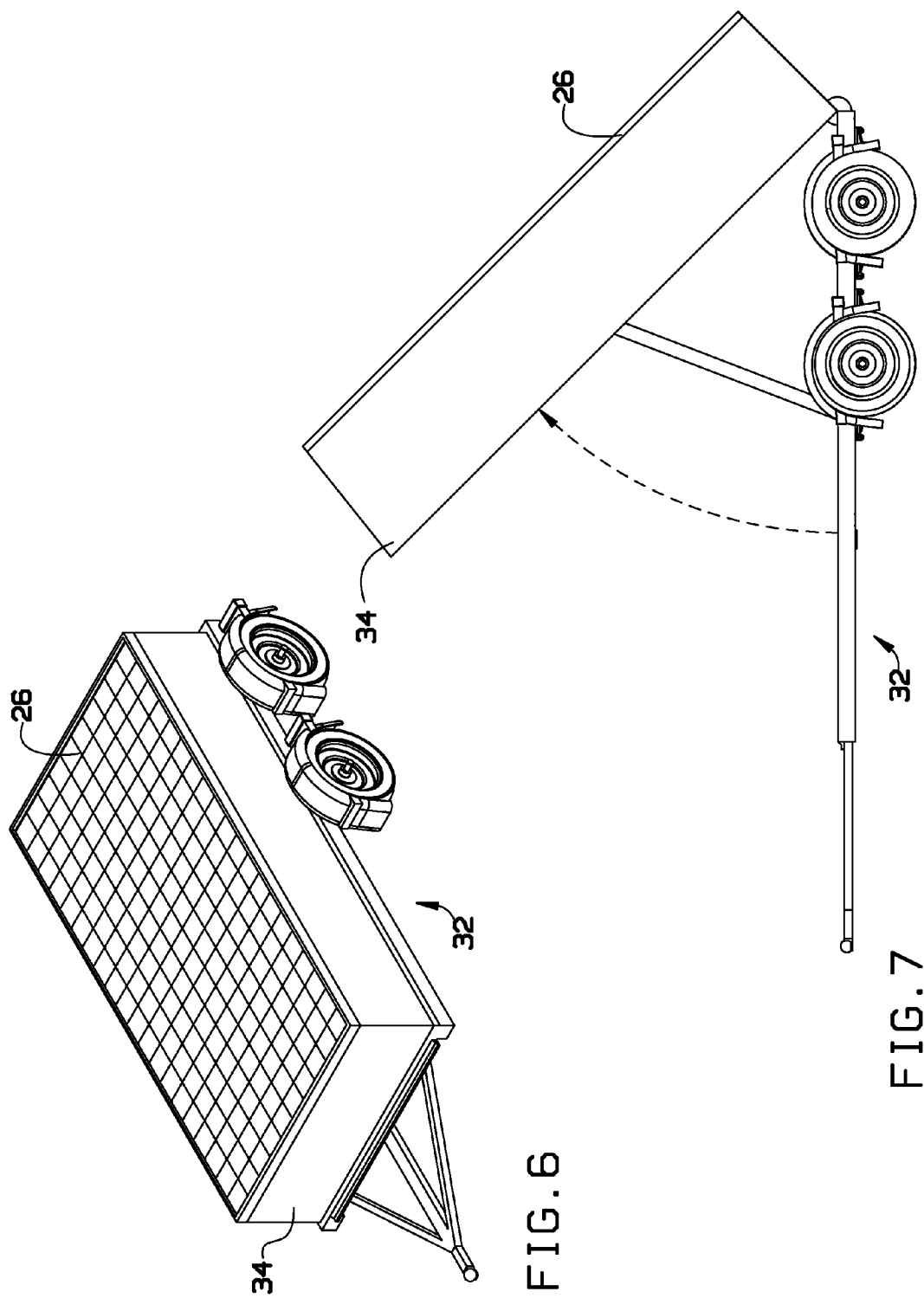
FIG. 6 is a perspective view of the invention of an alternate embodiment of the invention.
FIG. 7 is a side view of an alternate embodiment of the invention shown with item 34 trailer bed in rotated configuration.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a tank or bed having a plurality of sidewalls that create a bed cavity. A Fresnel panel frame that includes at least one Fresnel panel may be adjacent to the bed cavity and may cover at least a portion of the bed cavity. An amount of sludge may be contained within the bed cavity. When placed in sunlight, the heat enhanced by the Fresnel panels may heat the sludge sufficiently for the sludge to be used as fertilizer.

The present invention may provide solutions that may reduce municipality budgets for disposal of biosolids by saving on transportation and other disposal costs, while reducing the carbon footprint. The present invention is an innovative, proprietary and cost effective way to remove biosolids from wastewater treatment facilities with a large reduction in the biosolids disposal budget. The present invention may provide a method and apparatus for turning biosolids into Class AA organic fertilizer without risking the health of people or causing environmental damage. With the use of Fresnel panels, sunlight may be captured and thereby a sufficient amount of heat may thicken and/or process wastewater biosolids, septic waste and landfill leachate to produce a safe organic Class AA fertilizer. Further, the present invention may reduce the volume of the biosolids, septic waste and leachate by up to about 90% to about 99%.

Referring now to FIGS. 1 through 7, the present invention may include a tank or a bed 10. The bed 10 may be enclosed by a plurality of walls. The plurality of walls may include a first end wall 38, a second end wall 40, a first sidewall 42, and a second sidewall 44. The plurality of walls may create a bed cavity 12. The bed cavity 12 may be configured to contain sludge 24.

The sludge 24 may be pumped or dumped into the bed cavity 12. The sludge 24 may include, but is not limited to, wastewater sludge (biosolids), septic waste, landfill leachate, and the like. In certain embodiments, the sludge 24 may be pumped into the bed cavity 12 by a piping. However, the sludge 24 may be shoveled or dumped into the bed cavity through a top opening as well.

In certain embodiments, the bed cavity 12 may include multiple compartments. The bed cavity 12 may include multiple compartments by way of a bed cavity divider 14. The bed cavity divider 14 may include walls that separate sections of the bed cavity 12. As illustrated in FIGS. 1, 3 and 4, the bed cavity divider 12 may divide the bed cavity 12 into two different sections or compartments. Multiple compartments within the bed cavity 12 may allow a user to include multiple stages of sludge 24 treatment.

The present invention may include a Fresnel panel frame 20. The Fresnel panel frame 20 may include at least one Fresnel panel 30. In certain embodiments, the Fresnel panel frame 20 may include a plurality of Fresnel panels 30. The Fresnel panel frame 20 may be positioned adjacent to the plurality of sidewalls. In certain embodiments, the Fresnel panel frame 20 may rest or be attached to the top of the plurality of sidewalls. Thereby, the Fresnel panel frame 20 may at least partially cover the bed cavity 12. In certain embodiments, the Fresnel panel frame 20 may substantially cover the bed cavity 12 and in other embodiments, the Fresnel panel frame 20 may entirely cover the bed cavity 12.

The Fresnel panels 30 may be used to heat the sludge 24 and thereby turn the sludge 24 into usable and safe fertilizer. Sunlight 36 may pass through the Fresnel panels 30 and sufficiently heat the sludge 24. In certain embodiments, the Fresnel panels 30 may be used to heat the sludge 24 for about 24 hours to about 72 hours to change theسludge 24 into the usable fertilizer. However, in certain circumstances, the sludge 24 may be treated for shorter or longer periods of time. For example, if there is a larger amount of sludge 24 to be treated or the sludge 24 contains more water than average, the sludge 24 may take a longer amount of time stated.

The Fresnel panels 30 may include a spot Fresnel panel 26, a linear Fresnel panel 28 or the like. As illustrated in FIG. 3, the Fresnel panel frame 20 may include the linear Fresnel panels 28. As illustrated in FIG. 6, the Fresnel panel frame 20 may include the spot Fresnel panels 26.

In certain embodiments, the present invention may include a Fresnel sliding panel assembly 18. The Fresnel sliding panel assembly 18 may enable a user to move the Fresnel panel frame 20 to different orientations to cover different areas of the bed cavity 12. In certain embodiments, the plurality of walls may include bed rails 16 in certain configurations of the Fresnel sliding panel assembly 18. As illustrated in FIGS. 1 and 3, the bed rails 16 may be located on top of the edge of the first side wall 42 and the second side wall 44. A roller wheel 22 may be attached to the Fresnel panel frame 20.

The roller wheel 22 may align with and be positioned on the bed rail 16. In such embodiments, the Fresnel panel frame 20 may be moved along the bed rail 16. Thereby, the Fresnel panel frame 20 may be in an orientation where the Fresnel panels 30 are closer to the first end 38 and the Fresnel panel frame 20 may be in an orientation where the Fresnel panels 30 are closer to the second end 40. The sliding panel assembly 18 may be automatic or manual. Therefore, a user may physically move the Fresnel panel frame 20 from one side to the other or an activated machine may move the Fresnel panel frame 20 from one side to the other. While in use, the Fresnel panel frame 20 may be moved from the first end 38 to the second end 40 after about 24 hours to about 72 hours.

In certain embodiments, the tank or bed 10 may include a material turner or mixer. The turner or mixer may include at least one rod aligned at the bottom of the bed. The at least one rob may include ridges. The rod may also be powered or rotated manually. When the at least one rod is rotated, the sludge may turn and mix. This process may induce faster drying. It is envisioned that other turners and mixers may be used to serve the same purpose, and are thereby encompassed herein.

Once the sludge 24 has been dried and processed into fertilizer, the fertilizer may be removed from the tank or bed 10 manually or by machine. For example, a removal machine may be attached directly to the bed 10 and may remove the fertilizer when activated. The fertilizer may be bagged and sold as Class AA organic fertilizer.

In certain embodiments, the present invention may be mounted on a trailer bed 34 or directly on a vehicle. This may allow for easy transportation of the processed sludge 24. As illustrated in FIGS. 6 and 7, the present invention may include a trailer configuration 32. In such embodiments, once the sludge 24 has been processed into fertilizer, the fertilizer may easily be dumped into the desirable location.

Figure 8:
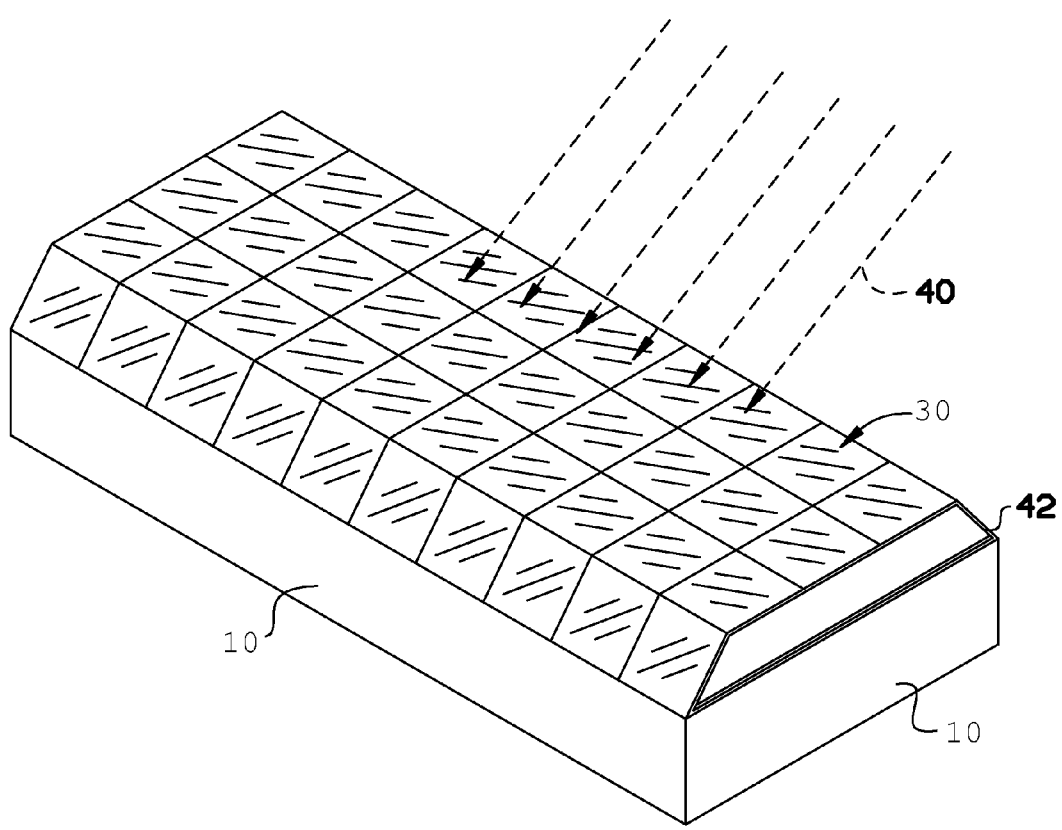
FIG. 8 is a perspective view of an alternate embodiment of the invention.

FIG. 8 provides an alternative embodiment of the present invention. The Fresnel panel frame 20 with a plurality of Fresnel panels 30 may be fixed to the bed 10. The Fresnel panels 30 adjacent to the sidewalls may be oriented at an angle relative to the sidewalls, while Fresnel panels 30 on the top may be parallel with the bed 10. In such embodiments, there may be an opening 42 to load and unload the sludge. Once the sludge has been loaded, exemplary solar radiation 40 may heat up the sludge and turn the sludge into fertilizer.

A user may build or machine the treatment/processing tank or bed 10. In certain embodiments, the bed 10 sidewalls may be about 24 to about 36 inches tall. The bed cavity 12 may include a holding capacity of around 7,000 gallons per chamber. In certain embodiments, the Fresnel panel frame 12 may cover half of the bed cavity 12. In certain embodiments, the tank may be exposed or may include a glass or polymer cover, such as Plexiglass®. In such embodiments, the half of that is not covered by the Fresnel Panels 20 may still be covered by the polymer cover.

A method of using the present invention may include the following. The sludge 24 material may be placed within the bed cavity 12. The Fresnel panel frame 20 with at least one Fresnel panel 30 may cover the bed cavity 12 at least partially. The sunlight may pass through the at least one Fresnel panel 30 and heat the sludge 24. The Fresnel panel frame 20 may then slide from one side to the other to process two batches. The sludge may be dried and pasteurized. After full processing, fertilizer may then be removed.

It should be understood, of course, that the foregoing relates to exemplary embodiments of the invention and that modifications may be made without departing from the spirit and scope of the invention as set forth in the following claims.

What is claimed is:

1. A system for changing sludge into fertilizer comprising:
   a bed comprising at least one sidewall forming a bed cavity configured to hold sludge; and
   at least one Fresnel panel configured to receive sunlight, wherein the at least one Fresnel panel covers at least a portion of the bed cavity, and is thereby configured to cover at least a portion of the sludge within the bed cavity,
   wherein the sunlight passes through the at least one Fresnel panel, thereby heating and converting the sludge into fertilizer.

2. The system of claim 1, further comprising a Fresnel panel frame containing the at least one Fresnel panel.

3. The system of claim 1, further comprising at least one bed cavity divider wall within the bed cavity creating at least two compartments within the bed cavity.

4. The system of claim 2, further comprising a Fresnel sliding panel assembly.

5. The system of claim 4, wherein the Fresnel sliding panel assembly comprises:
   a bed rail on the top edge of the at least one sidewall; and
   a roller wheel attached to the Fresnel panel frame,
   wherein the roller wheel aligns with and rests within the bed rail.

6. The system of claim 1, wherein the at least one Fresnel panel is at least one spot Fresnel panel.

7. The system of claim 1, wherein the at least one Fresnel panel is at least one linear Fresnel panel.

8. The system of claim 1, further comprising a trailer bed supporting the bed of the apparatus.

9. The system of claim 2, wherein the Fresnel panel frame comprises a plurality of Fresnel panels.

* * * * *